United States Patent [19]
Kunig

[11] Patent Number: 5,810,011
[45] Date of Patent: Sep. 22, 1998

[54] METHOD AND APPARATUS FOR MEASURING MYOCARDIAL IMPAIRMENT AND DYSFUNCTIONS FROM EFFICIENCY AND PERFORMANCE DIAGRAMS

[76] Inventor: Sabine Vivian Kunig, P.O. Box 192, Saltsburgh, Pa. 15681

[21] Appl. No.: 607,789

[22] Filed: Feb. 27, 1996

[51] Int. Cl.[6] ........................................ A61B 5/02
[52] U.S. Cl. .............................................. 128/668
[58] Field of Search ........................ 128/668, 691, 128/713, 672

[56] References Cited

U.S. PATENT DOCUMENTS

| | | | |
|---|---|---|---|
| 5,046,502 | 9/1991 | Kunig | 128/668 |
| 5,370,122 | 12/1994 | Kunig et al. | 128/668 |
| 5,584,298 | 12/1996 | Kabal | 128/677 |

Primary Examiner—William E. Kamm
Assistant Examiner—George R. Evanisko
Attorney, Agent, or Firm—Clifford A. Poff

[57] ABSTRACT

A diagnostic and monitoring device is used to diagnose myocardial impairment, dysfunctions, and the state of critical illness. The device has utility to design and monitor therapies for differential treatment of myocardial impairment, dysfunctions, rehabilitation, and conditioning exercises. Ventricular size, pressures, and heart rate are measured to determine cardiac efficiency given by volume and pressure efficiency components, cardiac work and myocardial oxygen consumption, the data being displayed in efficiency and performance diagrams to diagnose myocardial impairment from cardiac efficiency data, dysfunctions from myocardial oxygen consumption data, and the state of critical illness from cardiac work data.

19 Claims, 5 Drawing Sheets

METHOD AND APPARATUS FOR MEASURING MYOCARDIAL IMPAIRMENT AND DYSFUNCTIONS FROM EFFICIENCY AND PERFORMANCE DIAGRAMS

BACKGROUND OF THE INVENTION

1. Field of the Invention

The present invention relates to a cardiac monitor and, more specifically, to a method and apparatus for diagnosis of the degree of myocardial impairment, dysfunction, and the state of critical illness of a subject from efficiency and performance diagrams.

2. Description of Prior Art

Present hemodynamic evaluation of a subject includes the measurement of a plurality of parameters such as cardiac pressure, heart rate, cardiac output, and pulmonary and vascular resistance and a determination whether these parameters fall into an empirically established normal range. Each parameter is representative of only a specific aspect of the entire cardiocirculatory system. Therefore, hemodynamic measurements fail to provide an over-all assessment of the system due to the absence of the synergy of the measured data. Ambiguous diagnosis may result from these types of hemodynamic measurements.

Disclosed in U.S. Pat. No. 5,370,122 is a method and an apparatus to establish the synergy of measured parameters in the form of cardiac pressure-size curves. Deviations of instant pressure-size curves from basal pressure-size curves produce changes in the numerical values of cardiac efficiency, indicative of myocardial impairment, and in the numerical values of cardiac work, indicative of dysfunctions. Not disclosed in the '122 patent, however, is the synergy of cardiac efficiency, myocardial oxygen consumption and cardiac power into a single reference frame allowing for diagnosis of dysfunctions, myocardial impairments and critical illness.

It is an object of the present invention to provide an efficiency diagram for diagnosing myocardial impairment and facilitating the design of therapies affecting myocardial impairment and for monitoring the efficacy of these therapies.

It is another object of the present invention to determine more specifically pressure efficiency and volume efficiency from the efficiency diagram to differentially design and/or monitor the efficacy of therapies affecting pressure efficiency and volume efficiency for improvement of cardiac efficiency.

It is still another object of the present invention to provide a performance diagram for diagnosing dysfunctions and critical illness to allow the design of therapies affecting dysfunctions and the critical illness and/or the monitoring of these therapies.

SUMMARY OF THE PRESENT INVENTION

According to the present invention there is provided a cardiac diagnostic device for diagnosis of myocardial impairment, dysfunctions, and critical illness. The device provides means for producing and measuring signals representative of ventricular size, pressures, time intervals of heart beat, and heart rate from a subject, means for processing said signals, means to determine efficiency and performance diagrams from the processed signals, means for determining pressure, volume, and cardiac efficiencies from the efficiency diagram for diagnosing myocardial impairment, means for determining cardiac work, ventricular energy, and myocardial oxygen consumption for diagnosing dysfunctions and critical illness from the performance diagram, means for standardizing ventricular work and ventricular energy and ventricular myocardial oxygen consumption with respect to preselected reference values, and means such as audible or visual signals to alert upon the attainment of specific levels of myocardial impairment and dysfunctions or critical illness.

BRIEF DESCRIPTION OF THE DRAWINGS

The present invention will be more fully understood in conjunction with the detailed description of the accompanying drawings in which.

DETAILED DESCRIPTION OF THE PREFERRED EMBODIMENT

Figure 1:
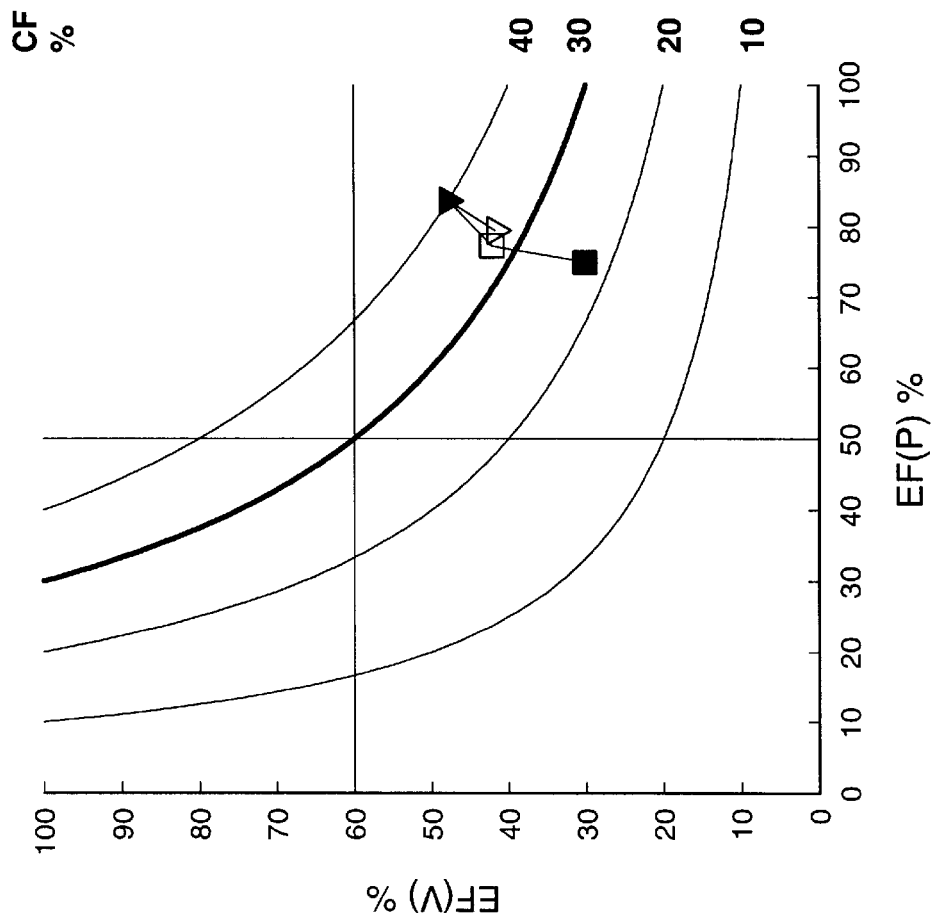
FIG. 1 illustrates an efficiency diagram used to determine cardiac efficiencies and its components volume efficiency and pressure efficiency for diagnosing myocardial impairment.

As disclosed in U.S. Pat. No. 5,370,122, cardiac work per one heart beat (W) is given by the equation:

$$W = (EDVI - ESVI) * (SBP - EDP) \quad (1)$$

where:
EDVI is the end-diastolic volume index,
ESVI is the end-systolic volume index,
SBP is the systolic blood pressure, and
EDP is the end-diastolic pressure.

EDVI and ESVI may be expressed as the ratio of end-diastolic volume, EDV/BSA and end-systolic volume ESV/BSA where BSA is the body surface area. Cardiac efficiency (CF) is given by the ratio of cardiac work (W) and the ventricular energy available for conversion to work (EDVI*SBP)

$$CF = (EDVI - ESVI)/EDVI * (SBP - EDP)/SBP \quad (2)$$

which may be rewritten as $$CF = EF(V) * EF(P) \quad (3)$$

where $EF(V) = (EDVI - ESVI)/EDVI$ is the volume efficiency and $EF(P) = (SBP - EDP)/SBP$ is the pressure efficiency.

Cardiac work expended during the time of one heart beat is given by the ratio of W and the time required for one beat (RR). Similarly, cardiac work per minute (CP) is given by the product of W and heart rate (HR).

$$CP = W * HR \quad (4)$$

Combining equations (1), (2), and (4) yields $$CP = CF * EDVI * SBP * HR \quad (5)$$

which indicates that a fraction (CF) of the available ventricular energy per minute, EDVI*SBP*HR, is converted to expend CP. It is noted that 1 liter of oxygen is consumed for the liberation of 4.82 kcal of energy. This relation allows conversion of EDVI*SBP*HR into myocardial oxygen consumption ($MVO_2$) and, accordingly, $$CP = CF * MVO_2 \quad (6)$$

subject to a conversion factor.

Inserting data published for normals at rest in Ciba-Geigy Scientific Tables, Ciba-Geigy Corporation, Medical Education Division, West Caldwell, N.J. 07006, ISBN 0-914168-54-1, 1990 yields basal values, for example, for the right heart EF(V)=60%, EF(P)=50%, CF=30%, and CP=$0.71*10^6$ erg/$m^2$*sec and for the left heart EF(V)=63%, EF(P)=93%, CF=60% and CP=$6.38*10^6$ erg/$m^2$*sec. These basal CP values are used as standards for right and left ventricle (heart), respectively, and assigned a unit of 1 CMET/sec. As a corollary, life cannot be sustained if the basal CP is not expended. A patient becomes critically ill if CP<1 CMET/sec. All present readings for a subject are presented as a multiple of 1 CMET/sec.

Inserting the basal values CF=30% and CP=1 CMET/sec for the right heart into equation 6 yields $RMVO_2$=3.33 CMET/sec which is the basal myocardial oxygen consumption of the right ventricle. Upon the occurrence of a dysfunction, CP expenditure increases to compensate said dysfunction, which, according to equation (6), requires $MVO_2$ to increase. As a corollary, $MVO_2$ greater than the basal value of 3.33 CMET/sec diagnoses a dysfunction.

Referring now to FIG. 1, in an efficiency diagram volume efficiency is plotted versus pressure efficiency. Curves are added to interconnect points in the efficiency diagram having equal values of the product EF(V) and EF(P) or equal values of CF, according to equation (3). Further, basal values of volume and pressure efficiency are added to the efficiency diagram as horizontal and vertical lines. The bold CF curve in FIG. 1 indicates basal cardiac efficiency, for example, for the right ventricle, for which CF=30%. A myocardial impairment exists if CF does not attain values as indicated by the basal CF curve. As will be apparent to those skilled in the art, the cardiac efficiency diagram for the left heart will have a basal cardiac efficiency, for example, of CF=60% and a plurality of similar curves for the left heart having different values for efficiency and myocardial oxygen consumption may be shown in a similar manner for that displayed in the right heart in FIG. 1. The efficiency diagram curves can be produced either as a function of the computer program or as a transparent overlay on the monitor.

Figure 2:
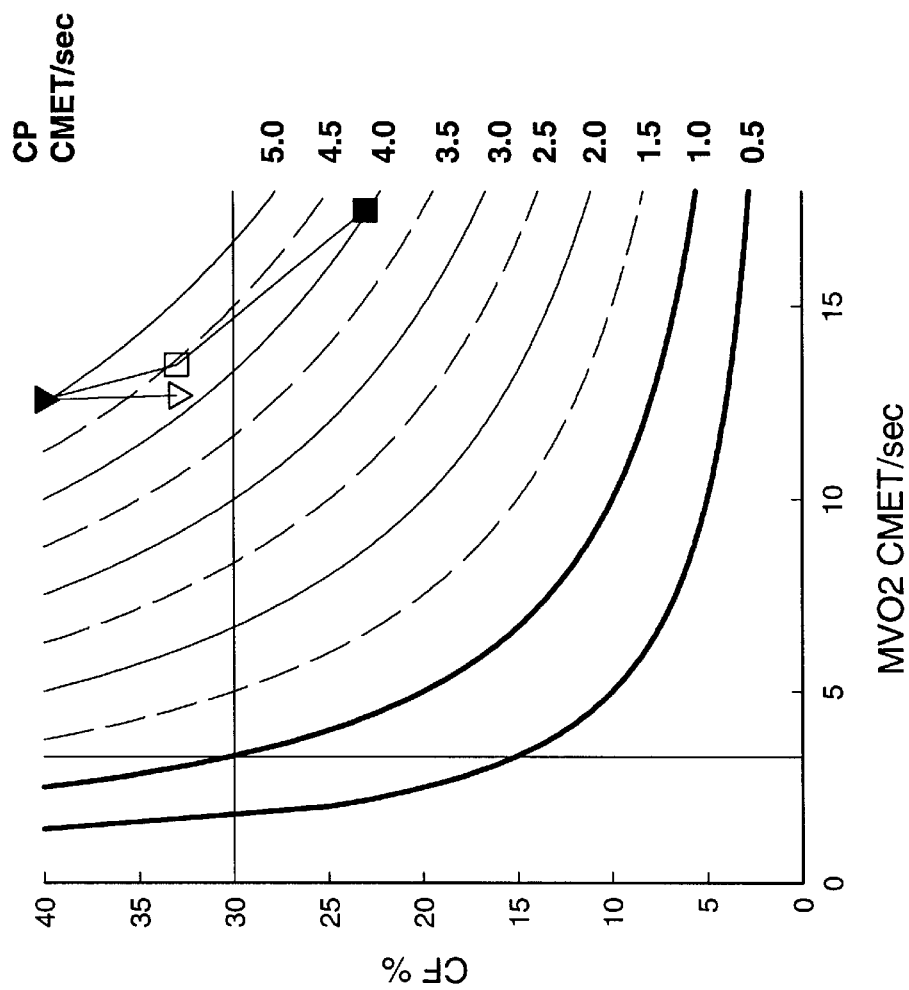
FIG. 2 illustrates a performance diagram used to determine ventricular energy, its metabolic equivalent of myocardial oxygen consumption, and cardiac work for diagnosing dysfunctions and the state of critical illness.

Referring now to FIG. 2, in a performance diagram CF is plotted versus EDVI*SBP*HR or, alternatively, versus $MVO_2$. Curves are added to interconnect points in the performance diagram having equal values of CP. Further, basal values for CF and $MVO_2$ are added as horizontal and vertical lines. A myocardial impairment exists below the horizontal line, a dysfunction exists to the right of the vertical line, and a patient is critically ill in the zone defined by the CP=1 CMET/sec curve and the CP=0.5 CMET/sec curve. The patient is near death when approaching CP=0.5 CMET/sec curve. The curves of the performance diagram can be produced either as a function of the computer program or as a transparent overlay on the monitor.

Figure 3:
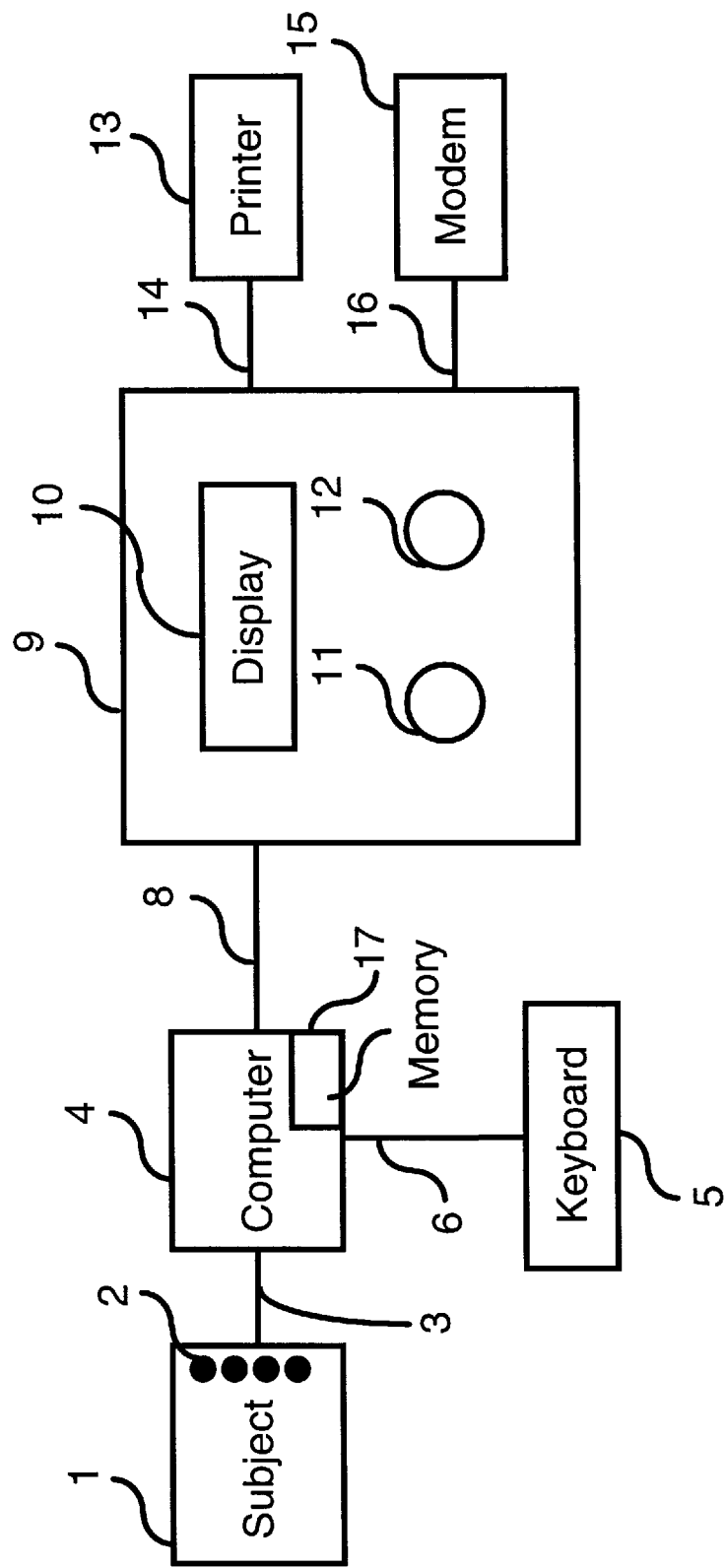
FIG. 3 shows a block diagram of the apparatus to practice the instant invention.

The embodiment, as shown in FIG. 3 illustrates the teachings of the instant invention. Accordingly, sensors 2 are placed on a subject 1 to detect signals representative of end-diastolic volume, end-systolic volume, systolic blood pressure, end-diastolic blood pressure, time for one heart cycle, and heart rate which are transmitted on multi-line wire 3 to computer 4. Such sensors 2 may include catheters, ultra-sound equipment, and pressure transducers as required for differential assessment of the left or right heart. Additional input representative of patient information including weight, height, body surface area, and preselected basal values is provided from a keyboard 5 to computer 4 on line 6. Computer 4 is programmed to process all incoming signals for determination of volume efficiency, pressure efficiency, cardiac efficiency, cardiac work, ventricular energy, and ventricular myocardial oxygen consumption, said parameters being transmitted by line 8 to a monitor 9 which is comprised of a display 10, audible and visual alarms 11 to warn of emergencies if preset values of the parameters are attained, and indicators 12 to diagnose myocardial impairment, dysfunction, and critical illness from the attainment of specific values of cardiac efficiency, myocardial oxygen consumption, and cardiac work. Inputs from keyboard 5 may be used to select from among the various diagrams for display by display 10 along with plotted points representing instant conditions of a monitored subject. The signal displayed by display 10 and the audio and visual alarms 11 and the signals displayed by indicator 12 are transmitted on line 14 to a printer 13 for producing hard copies and on line 16 to a modem 15 for transmission over telephone lines to central storage. A memory 17 in the computer 4 serves as storage of all information and data.

Referring now to FIGS. 1 and 2 collectively, data shown in Table 1, as published by J. W. Biondi, et al. in an article entitled *The Effect of Incremental Positive End-Expiratory Pressure on Right Ventricular Hemodynamics and Ejection Fraction,* Anesthesia Analgesia 1988; 67:144–151, on patients with acute respiratory disease are used to demonstrate the utility of efficiency and performance diagrams to diagnose myocardial impairment, dysfunction, and critical illness from right ventricular data.

TABLE 1

| PEEP | | 0 cm $H_2O$ ▽ | 5 cm $H_2O$ ▼ | 10 cm $H_2O$ □ | 20 cm $H_2O$ ■ |
|---|---|---|---|---|---|
| SBP | mm Hg | 39 | 43 | 44 | 48 |
| EDP | mm Hg | 6 | 7 | 6 | 8 |
| EDVI | ml/$m^2$ | 103 | 92 | 95 | 113 |
| ESVI | ml/$m^2$ | 60 | 48 | 55 | 79 |
| HR | 1/min | 101 | 102 | 103 | 103 |
| EF(V) | % | 42 | 48 | 42 | 30 |
| EF(P) | % | 79 | 84 | 77 | 75 |
| CF | % | 33 | 40 | 32 | 23 |
| $MVO^2$ | CMET/sec | 12.7 | 12.6 | 13.5 | 17.6 |
| CP | CMET/sec | 4.2 | 5.1 | 4.4 | 3.9 |

These patients were treated with positive end-expiratory pressures (PEEP) of varying magnitudes indicated by the symbols ▽ no PEEP, ▼ 5 cm $H_2O$ PEEP, □ 10 cm $H_2O$ PEEP, and ■ 20 cm $H_2O$ PEEP. The computer 4 receives input signals representative of EDVI, ESVI, SBP, EDP, and HR, processes them to determine EF(V), EF(P), CF, $RMVO_2$, and CP. Subsequently, computer 4 generates a performance and an efficiency diagram. According to the teachings of the instant invention, the cardiac monitor of FIG. 3 by displaying a performance diagram of FIG. 1 reveals a dysfunction (in this case a respiratory disease) as $RMVO_2$ significantly exceeds the basal $RMVO_2$. No myocardial impairment is revealed by the cardiac monitor for no PEEP treatment and for PEEP treatments not exceeding 10 cm H2$_O$ since cardiac efficiencies for the respective treatments exceed the basal cardiac efficiency below which impairment is indicated. Still further, the cardiac monitor reveals a PEEP of 5 cm H$_2$O as the most beneficial pressure to elevate cardiac efficiency to its highest levels.

In another aspect of the teachings of the present invention the cardiac device of FIG. 3 by displaying an efficiency diagram of FIG. 1, containing a data point representing an instant condition of a monitored subject, reveals depressed volume efficiencies which are compensated by elevated pressure efficiencies to result in an over-all normal cardiac efficiency for no PEEP treatment and PEEP treatments not exceeding 10 cm H$_2$O. The cardiac monitor also detects a concomitant volume efficiency and pressure efficiency deterioration for PEEP of 20 cm H$_2$O resulting in an abnormally low cardiac efficiency representative of myocardial impairment. The cardiac monitor, thus, allows the design of specific therapies affecting myocardial impairment through volume efficiency and pressure efficiency, and design of therapies affecting dysfunctions and the monitoring of these therapies.

In still another embodiment of the present invention representations of CF in form of EF(V), EF(P), and EF(A) =(EDAI–ESAI)/EDAI and representations of MVO$_2$ in form of EDVI*HR, SBPI*HR, where SBPI equals the ratio of pressure to body surface area, EDAI*SBP*HR, where EDAI equals the end-diastolic cross-sectional area referenced to BSA of the ventricle end ESAI=the end-systolic cross-sectional area referenced to BSA may be used, respectively, for the left heart and the right heart, as well as the substitution of ventricular pressures by arterial pressures, right ventricular pressure by pulmonary artery pressure or central venous pressure, left ventricular systolic pressure by arterial systolic and left ventricular diastolic pressure by wedge pressure or arterial diastolic pressure to determine efficiency and performance diagrams for right and left ventricles.

Referring now to Table 2, there are listed heart rate and blood pressure data as published by R. A. Wolthuis et. al. in an article entitled, *The response of healthy men to treadmill exercise,* Circulation 1977;55:153–157, which were used to determine left ventricular myocardial oxygen consumption and pressure efficiency to practice the instant invention to design and monitor rehabilitation and conditioning exercise programs.

TABLE 2

| Age | | | 26 years | 47 years |
|---|---|---|---|---|
| BSA | [m$^2$] | rest | 1.77 | 2.13 |
| SBP | [mm Hg] | rest | 115 | 140 |
| SBP(1) | [mm Hg] | sub-maximal | 132 | 174 |
| SBP(2) | [mm Hg] | sub-maximal | 148 | 193 |
| SBP(3) | [mm Hg] | sub-maximal | 160 | 208 |
| SBP | [mm Hg] | maximal | 164 | 216 |
| EDP | [mm Hg] | rest | 80 | 90 |
| EDP(1) | [mm Hg] | sub-maximal | 68 | 90 |
| EDP(2) | [mm Hg] | sub-maximal | 65 | 90 |
| EDP(3) | [mm Hg] | sub-maximal | 60 | 90 |
| EDP | [mm Hg] | maximal | 60 | 96 |
| HR | [1/min] | rest | 60 | 82 |
| HR(1) | [1/min] | sub-maximal | 102 | 141 |
| HR(2) | [1/min] | sub-maximal | 130 | 174 |
| HR(3) | [1/min] | sub-maximal | 158 | 190 |
| HR | [1/min] | maximal | 200 | 188 |
| EF(P) | [%] | rest | 30 | 36 |
| EF(P) (1) | [%] | sub-maximal | 48 | 48 |
| EF(P) (2) | [%] | sub-maximal | 56 | 53 |
| EF(P) (3) | [%] | sub-maximal | 63 | 57 |

TABLE 2-continued

| Age | | | 26 years | 47 years |
|---|---|---|---|---|
| EF(P) | [%] | maximal | 63 | 56 |
| MVO$_2$ | [CMET/sec] | rest | 3.33 | 4.43 |
| MVO$_2$(1) | [CMET/sec] | sub-maximal | 6.25 | 9.46 |
| MVO$_2$(2) | [CMET/sec] | sub-maximal | 8.93 | 13.0 |
| MVO$_2$(3) | [CMET/sec] | sub-maximal | 11.73 | 15.2 |
| MVO$_2$ | [CMET/sec] | maximal | 13.3 | 15.7 |
| CP | [CMET/sec] | rest | 1.0 | 1.59 |
| CP | [CMET/sec] | sub-maximal | 3.0 | 4.54 |
| CP | [CMET/sec] | sub-maximal | 5.0 | 6.89 |
| CP | [CMET/sec] | sub-maximal | 7.39 | 8.66 |
| CP | [CMET/sec] | maximal | 8.38 | 8.79 |

Figure 4:
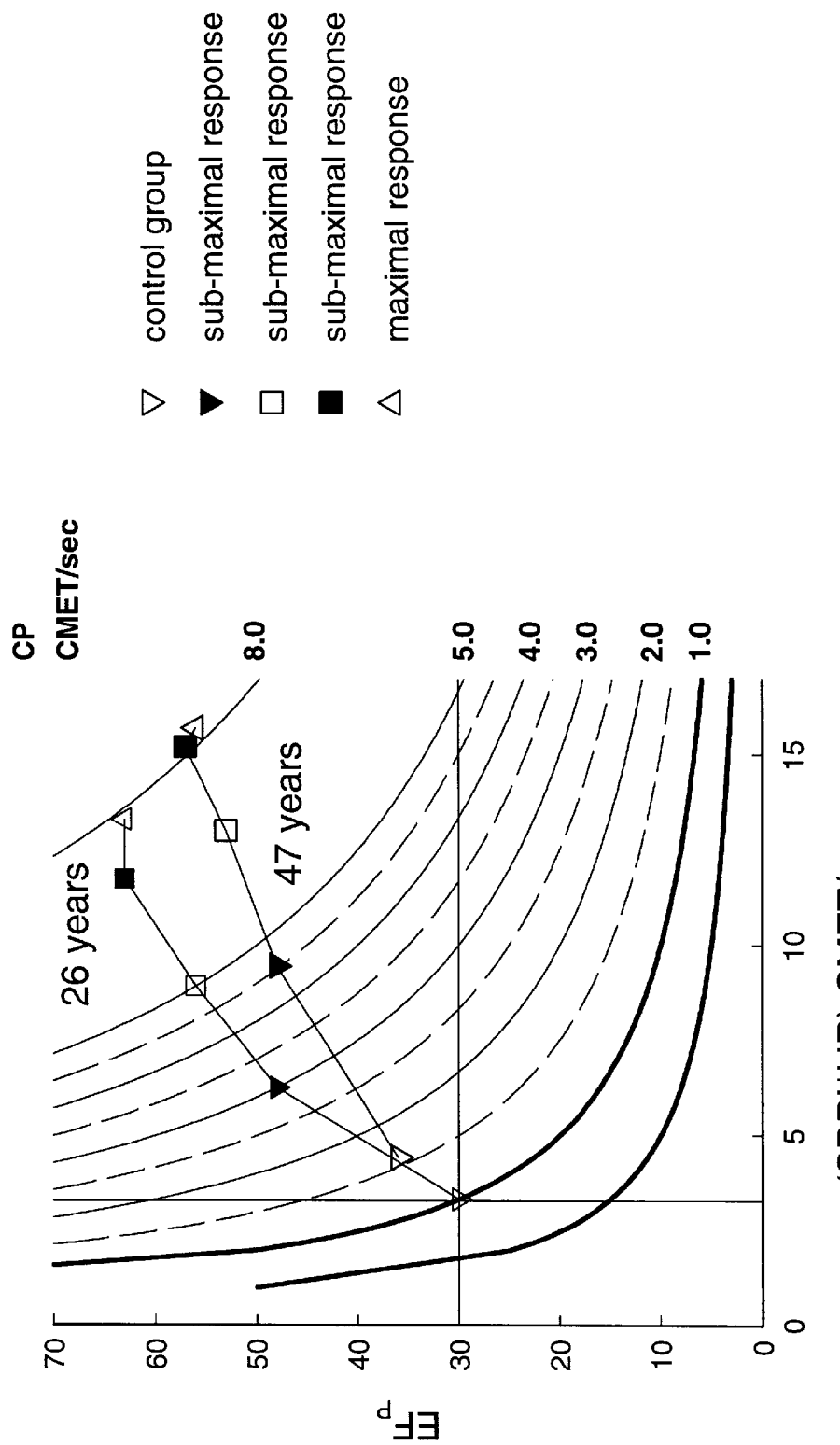
FIG. 4 illustrates the utility of the present invention to diagnose cardiac efficiency of an exercising subject, to design rehabilitation and exercising programs, and to determine the intensity levels for beneficial exercise.

Referring now to the performance diagram shown in FIG. 4, there is plotted pressure efficiency as a representation of cardiac efficiency and SBPI*HR as a representation of MVO$_2$ for the left heart for two groups of subjects of different ages exercising on a treadmill. The symbols denote time on the treadmill as follows ▽ at rest prior to commencement of the treadmill test, ▼ stage 1, sub-maximal response, □ stage 2 sub-maximal response, ■ stage 3 sub-maximal response, Δ maximal response. Subjects of the younger age group utilize a smaller amount of oxygen more efficiently as compared to the subject of older age. A threshold efficiency is attained prior to maximal exertion. Thus, the cardiac monitor of FIG. 3 allows the design of exercise programs, for example, for cardiac rehabilitation and for competitive athletes at the threshold of maximum efficiency to assure safety of cardiac patients and progress in the conditioning program of athletes.

Referring now to Table 3, there are listed heart rate and blood pressure data as published by A. S. Phillips et. al. in an article entitled *Propofol-Fentanyl anesthesia: A comparison with Isoflurane-Fentanyl anesthesia in coronary artery bypass grafting and valve replacement surgery,* Journal of Cardiothoracic and Vascular Anesthesia 1994;8:289–296, which were used to determine left ventricular myocardial oxygen consumption and pressure efficiency to practice the instant invention to design and monitor drug therapies such as anesthesia.

TABLE 3

| | | pre-anesthesia | post-anesthesia |
|---|---|---|---|
| BSA | [m$_2$] | 1.91 | 1.91 |
| HR | [1/min] | 61 | 65 |
| SBP | [mm Hg] | 127 | 105 |
| EDP | [mm Hg] | 66 | 60 |
| EF(P) | [%] | 48 | 43 |
| MVO$_2$ | [CMET/sec] | 3.33 | 2.94 |
| CP | [CMET/sec] | 1.6 | 1.26 |

Figure 5:
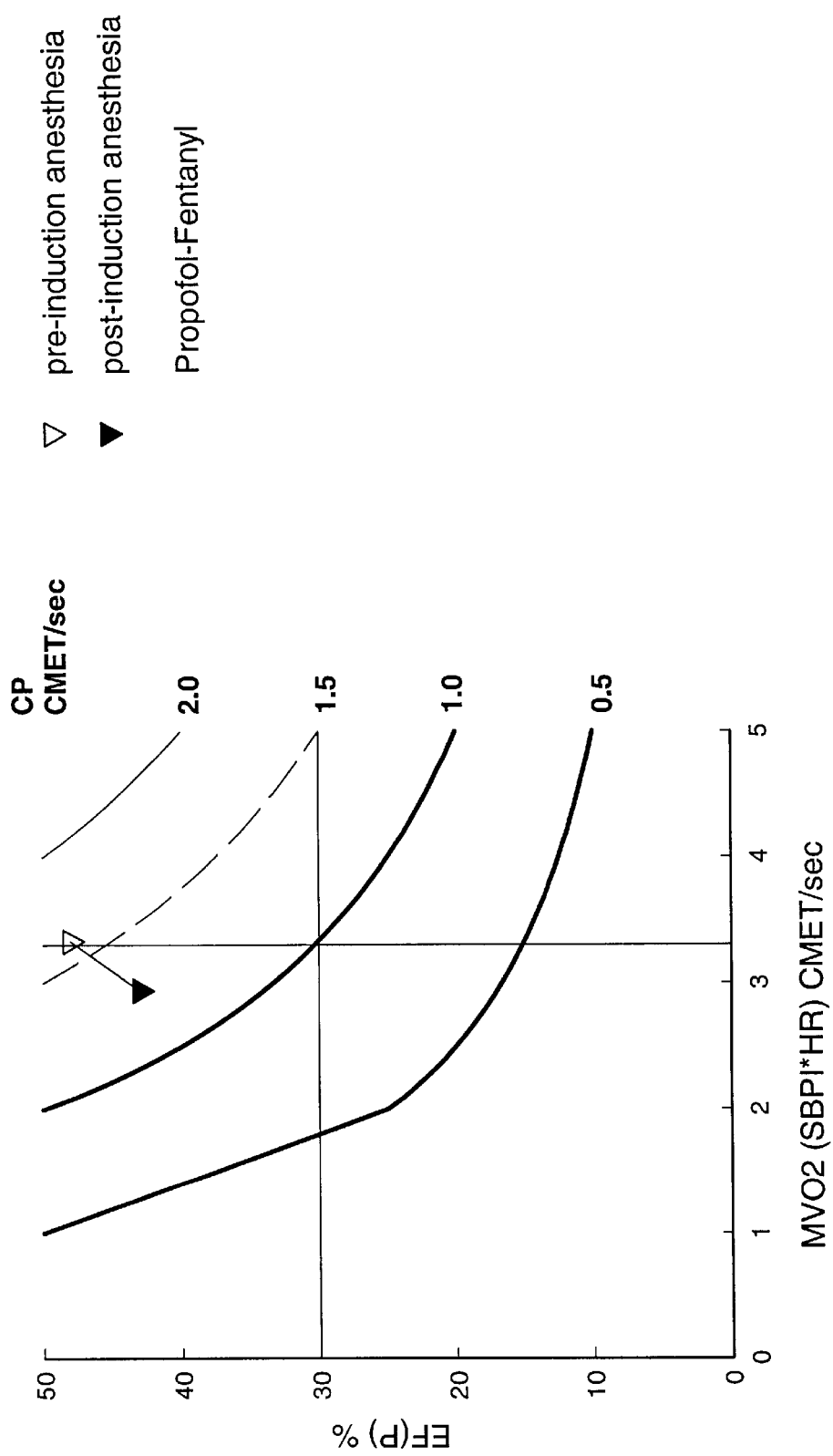
FIG. 5 illustrates the utility of the present invention to diagnose myocardial impairment and dysfunction, design and monitoring of therapies, and drug interventions.

Referring now to FIG. 5, there is shown the performance diagram, created by the monitor of FIG. 3 which uses data from Table 3, of a group of patients in whom anesthesia is administered, where ▽ denotes the state prior to anesthesia and ▽ the state after anesthesia administration by the drug Propofol-Fentanyl. The patient shows a decreased cardiac efficiency representative of myocardial impairment caused by the anesthesia. Thus, the cardiac monitor has utility to design therapies and monitor efficacy of therapies, drug interventions and the safety of patients.

In yet another embodiment numerous values for each of CF, MVO$_2$, CP and their representations may be collected and displayed in time reference frames including the time derivatives to further monitor progress or regress of myocardial impairments and dysfunctions.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

I claim:

1. A cardiac diagnostic device for monitoring a subject, said device including;
   means for measuring physiological parameters of such subject;
   means responsive to measurements of physiological parameters of such subject for deriving values of cardiac efficiency and myocardial oxygen consumption;
   means for establishing a boundary of physiological criticality in a first reference frame of cardiac efficiency versus myocardial oxygen consumption; and
   means using said cardiac efficiency and myocardial oxygen consumption of such subject for establishing a subject data point in said first reference frame whereby a comparison is allowed between said subject data point and said boundary of physiological criticality.

2. The cardiac diagnostic device according to claim 1 wherein said boundary of physiological criticality includes at least one curve in said first reference frame, said curve containing at least one reference point representing an absence of dysfunction and myocardial impairment.

3. The cardiac diagnostic device according to claim 2 wherein said means responsive to said measurements further derives cardiac pressure efficiency and cardiac volume efficiency for such subject;
   and wherein said means for establishing a boundary of physiological criticality further establishes at least one cardiac efficiency curve in a cardiac efficiency reference frame of cardiac volume efficiency versus cardiac pressure efficiency, said cardiac efficiency curve containing a basal reference point representing a basal value for cardiac volume efficiency and a basal value for cardiac pressure efficiency;
   and wherein said means for establishing a subject data point in said first reference frame further establishes a second subject data point in said cardiac efficiency reference frame using said derived cardiac pressure efficiency and cardiac volume efficiency whereby a comparison is allowed between said second subject data point and said cardiac efficiency curve for the left or right heart.

4. The cardiac diagnostic device according to claim 3 wherein said cardiac efficiency curve consists of a plurality of cardiac efficiency curves in said cardiac efficiency reference frame.

5. The cardiac diagnostic device according to claim 3 wherein said cardiac efficiency is defined as the product of cardiac volume efficiency and cardiac pressure efficiency.

6. The cardiac diagnostic device according to claim 3 wherein said cardiac efficiency curve represents a cardiac basal efficiency value for all values of cardiac volume efficiency and cardiac pressure efficiency.

7. The cardiac diagnostic device according to claim 3 further including using said subject data point and said curve in said first reference frame and second subject data point and said cardiac efficiency curve in said cardiac efficiency frame to design and monitor therapies for differential treatment of myocardial impairment or dysfunction.

8. The cardiac diagnostic device according to claim 3 further including using said subject data point and said curve in said first reference frame and second subject data point and said cardiac efficiency curve in said cardiac efficiency frame to design and monitor exercise programs for cardiac rehabilitation and conditioning of subjects.

9. The cardiac diagnostic device according to claim 2 wherein said means for establishing a boundary includes a second curve establishing a zone of physiological criticality with said at least one curve at which death is imminent.

10. the cardiac diagnostic device according to claim 2 wherein said at least one curve further establishes a basal level of cardiac work expended, and wherein said means for establishing further provides a plurality of curves representing elevated levels of cardiac work expended relative to said basal level.

11. The cardiac diagnostic device according to claim 1 wherein said measurements of physiological parameters include signals representative of ventricular size, ventricular blood pressure, time for completion of one cardiac cycle, and heart rate.

12. The cardiac diagnostic device according to claim 1 wherein said means responsive to physiological measurements of physiological parameters further derives volume efficiency, pressure efficiency, cardiac work and available energy for conversion to cardiac work.

13. A method of diagnosing myocardial impairments, dysfunctions and physiological criticality of a subject, said diagnostic method including the steps of:
   monitoring such subject to obtain measurements representative of physiological parameters;
   determining cardiac efficiency and myocardial oxygen consumption for such subject using said representative measurements;
   establishing a boundary of physiological criticality in a first reference frame of cardiac efficiency versus myocardial oxygen consumption;
   establishing a subject data point in said first reference frame which represents said determined cardiac efficiency and myocardial oxygen consumption for such subject; and
   comparing said subject data point with said boundary to indicate physiological criticality.

14. The method according to claim 13 including the further steps of:
   providing at least one curve in said first reference frame containing at least one reference point which represents an absence of dysfunction and myocardial impairment; and
   comparing said subject data point to said at least one curve to diagnose myocardial impairments and dysfunctions of the left or right heart of such subject using said reference point of said curve.

15. The method according to claim 14, wherein said diagnosis of impairment is made by comparing the position of said data point with said reference point with respect to said cardiac efficiency of said first reference frame, and wherein said diagnosis of dysfunction is made by comparing the position of said data point with said reference point with respect to said myocardial oxygen consumption of said first reference frame.

16. The method according to claim 14, including the further steps of:

determining cardiac pressure efficiency and cardiac volume efficiency for such subject using said representative measurements;

providing at least one cardiac efficiency curve in a cardiac efficiency reference frame of cardiac volume efficiency versus cardiac pressure efficiency, said cardiac efficiency curve containing an basal reference point representing a basal value for cardiac volume efficiency and a basal value for cardiac pressure efficiency;

establishing a second subject data point in said cardiac efficiency reference frame using said determined cardiac pressure efficiency and cardiac volume efficiency;

comparing said second subject data point with said cardiac efficiency curve to determine more specifically a cardiac condition and to aid in designing therapies affecting said impairments and dysfunctions.

17. The method according to claim 16 wherein said comparison of said second subject data point with said cardiac efficiency curve involves comparing the volume efficiency of said second subject data point with the basal volume efficiency and comparing the pressure efficiency of said second subject data point with the basal pressure efficiency.

18. The method according to claim 16 further including the step of designing and monitoring therapies, exercise rehabilitation programs in response to said step of comparing.

19. the cardiac diagnostic device according to claim 12, wherein said means for establishing further provides a plurality of progression curves each in one progress reference frame, each of said progression reference frames having one of said derived values versus time, said progression curves containing points representing instant values of said derived values or their time derivatives for such subject at different times during a therapy treatment or an exercise program.

* * * * *